United States Patent
Chang

(10) Patent No.: US 10,045,873 B2
(45) Date of Patent: Aug. 14, 2018

(54) KNEE TRACTION APPARATUS

(71) Applicant: Changeui Medical co., Ltd., Seoul (KR)

(72) Inventor: Ki Yong Chang, Seoul (KR)

(73) Assignee: Changeui Medical co., Ltd., Seoul (KR)

( * ) Notice: Subject to any disclaimer, the term of this patent is extended or adjusted under 35 U.S.C. 154(b) by 373 days.

(21) Appl. No.: 14/476,853

(22) Filed: Sep. 4, 2014

(65) Prior Publication Data

US 2015/0272768 A1    Oct. 1, 2015

(30) Foreign Application Priority Data

Mar. 25, 2014    (KR) ........................ 10-2014-0034837

(51) Int. Cl.
*A61F 5/01*    (2006.01)

(52) U.S. Cl.
CPC .... *A61F 5/0125* (2013.01); *A61F 2005/0137* (2013.01); *A61F 2005/0139* (2013.01); *A61F 2005/0165* (2013.01)

(58) Field of Classification Search
CPC .................. A61F 5/0123; A61F 5/0125; A61F 2005/0139; A61F 5/0102; A61F 2005/0167; A61F 5/0111; A61F 13/06; A61G 13/12; A61G 2013/0063

See application file for complete search history.

(56) References Cited

U.S. PATENT DOCUMENTS

| | | | | |
|---|---|---|---|---|
| 4,697,583 A * | 10/1987 | Mason | ................... | A61F 5/0123 602/16 |
| 5,443,444 A * | 8/1995 | Pruyssers | .............. | A61F 5/0123 602/16 |
| 7,311,687 B2 * | 12/2007 | Hoffmeier | ............. | A61F 5/0123 602/16 |

FOREIGN PATENT DOCUMENTS

| | | |
|---|---|---|
| JP | 2003-159267 A | 6/2003 |
| KR | 10-2010-0090619 | 8/2010 |
| KR | 10-2011-0026543 A | 3/2011 |

* cited by examiner

*Primary Examiner* — Ophelia A Hawthorne
(74) *Attorney, Agent, or Firm* — Casimir Jones, SC; Robert A. Goetz

(57) ABSTRACT

A knee traction apparatus may include an upper frame provided to be worn on a thigh region and including an upper fraction member disposed in an end of the upper frame, and a lower frame provided to be worn on a lower leg region and including a lower traction member that is disposed in an end of the lower frame and is to rotate in mesh with the upper traction member. The upper traction member and the lower traction member may be in contact with each other in front of a knee joint.

12 Claims, 16 Drawing Sheets

KNEE TRACTION APPARATUS

CROSS-REFERENCE TO RELATED APPLICATION

This application claims the benefit of Korean Patent Application No. 10-2014-0034837, filed on Mar. 25, 2014, in the Korean Intellectual Property Office, the disclosure of which is incorporated herein by reference.

BACKGROUND

1. Field of the Invention

The present invention relates to a knee traction apparatus, and more particularly, to a knee traction apparatus for protecting cartilages by reducing load applied to a knee.

2. Description of the Related Art

A joint refers to a location in which at least two bones forming a skeleton are connected, and all movements of a human body may be performed in joints. Joints enabling the above movements may be referred to as movable joints, and most of skeletons of a human body may be connected by movable joints.

A knee joint among various joints corresponds to a middle portion of a leg, and refers to a hinge joint between a lower end of a femur and an upper end of a tibia.

The knee joint may be involved in bending. Additionally, due to instability of a structure of bones of the knee joint, tissues other than joints, for example muscles, ligaments, joint membranes, and the like may contribute to stability of the knee joint.

However, bones, ligaments, and the like may be injured due to a degenerative change or injury of cartilages that protect joints, which may lead to inflammations and pain, that is, arthritis. When these symptoms persist, deformity of joints may be caused. In particular, degenerative arthritis of a knee may be a major cause of a chronic physical disorder.

Research has been conducted to treat the above arthritis, and Korean Patent Application No. 10-2010-0090619 filed in Jul. 13, 2009, discloses a knee brace detachably coupled to an ankle brace.

SUMMARY

An aspect of the present invention provides a knee traction apparatus in which a rotation axis of a traction member is located in front of a knee joint.

Another aspect of the present invention provides a knee fraction apparatus that may efficiently limit a bending angle of a knee joint, using a stopper.

Still another aspect of the present invention provides a knee traction apparatus that may reduce manufacturing costs and may facilitate manufacturing, since a connection member is located adjacent to a knee joint.

Yet another aspect of the present invention provides a knee traction apparatus that may protect cartilages by reducing load applied to a knee joint, may relieve pain of the knee joint, and may induce healing of the knee joint.

A further aspect of the present invention provides a knee traction apparatus that may support a knee joint so that a user may naturally straighten and bend a knee joint.

According to an aspect of the present invention, there is provided a knee traction apparatus including: an upper frame provided to be worn on a thigh region, and including an upper traction member disposed in an end of the upper frame; and a lower frame provided to be worn on a lower leg region, and including a lower traction member disposed in an end of the lower frame, the lower traction member rotating in mesh with the upper fraction member, wherein the upper traction member and the lower traction member are in contact with each other in front of a knee joint.

The upper frame may include an upper straight member extending from a side of the thigh region, and an upper diagonal member connecting the upper straight member and the upper traction member. The lower frame may include a lower straight member extending from a side of the lower leg region, and a lower diagonal member connecting the lower straight member and the lower traction member.

An end portion of each of the upper traction member and the lower traction member may have a saw-toothed shape, and the upper traction member and the lower traction member may rotate in mesh.

The knee fraction apparatus may further include a guide member in which a rotation axis of each of the upper traction member and the lower fraction member is located.

The upper frame may include an upper protruding element protruding inward from the upper frame, and the lower frame may include a lower protruding element protruding inward from the lower frame. The guide member may include a first guide groove to guide the upper protruding element inserted into the first guide groove, and a second guide groove to guide the lower protruding element inserted into the second guide groove. The upper protruding element and the first guide groove may be symmetrical to the lower protruding element and the second guide groove, respectively.

The first guide groove and the second guide groove may be located further behind the knee joint than the upper traction member and the lower traction member, respectively, and each may have a curved shape or a linear shape.

The guide member may further include a stopper installed in the first guide groove or the second guide groove, and a rotation angle between the upper frame and the lower frame may be limited by the stopper.

The knee traction apparatus may further include a cover to protect the upper traction member, the lower traction member, or the guide member.

According to another aspect of the present invention, there is provided a knee traction apparatus including: an upper frame provided to be worn on a thigh region, and including an upper traction member disposed in an end of the upper frame; and a lower frame provided to be worn on a lower leg region, and including a lower traction member disposed in an end of the lower frame, the lower traction member rotating in mesh with the upper traction member, wherein the upper frame includes upper straight members extending from both sides of the thigh region, and an upper connection member connecting the upper straight members, the lower frame includes lower straight members extending from both sides of the lower leg region, and a lower connection member connecting the lower straight members, and the upper connection member is formed between the other end of the upper frame and the upper traction member, and the lower connection member is formed between the other end of the lower frame and the lower traction member.

The upper traction member and the lower traction member may be in contact with each other in front of a knee joint.

According to another aspect of the present invention, there is provided a knee traction apparatus including: an upper frame provided to be worn on a thigh region, and including a first connector disposed in an end of the upper frame; and a lower frame provided to be worn on a lower leg region, and including a second connector rotating in contact with the first connector, wherein a contact area between the first connector and the second connector has an oval shape, the first connector and the second connector rotate in contact with each other while drawing oval tracks, and the first connector or the second connector moves toward a major axis of the oval track of the first connector or the second connector while a knee is straightened, and moves toward a minor axis of the oval track of the first connector or the second connector while the knee is bent.

An end portion of each of the first connector and the second connector may have a saw-toothed shape, and the first connector and the second connector may rotate in mesh.

The knee traction apparatus may further include a guide member mounted in the first connector and the second connector, to stably guide rotation of the first connector and the second connector.

The first connector may include a first protruding element protruding outward from a focal point of the first connector, and a third protruding element protruding inward from a central point of the first connector. The second connector may include a second protruding element protruding outward from a focal point of the second connector, and a fourth protruding element protruding inward from a central point of the second connector. The guide member may include an outer guide member to connect the first protruding element and the second protruding element, and an inner guide member to connect the third protruding element and the fourth protruding element.

The outer guide member may include a first groove into which the first protruding element is inserted, and a second groove into which the second protruding element is inserted. The first groove and the second groove may be aligned in the outer guide member and each may have a linear shape. The inner guide member may include a third groove into which the third protruding element is inserted, and a fourth groove into which the fourth protruding element is inserted. The third groove and the fourth groove may be aligned in the inner guide member and each may have a linear shape.

The first connector further may include a fifth protruding element disposed outside the first connector, and the second connector further may include a sixth protruding element is disposed outside the second connector. The outer guide member further may include a fifth groove into which the fifth protruding element is inserted and having a curved shape, and a sixth groove into which the sixth protruding element is inserted and having a curved shape.

The first connector and the second connector may be detachably coupled to the upper frame and the lower frame, respectively.

The knee traction apparatus may further include a cover to protect the first connector, the lower second connector, and the guide member. The cover may include a movement element connected to the first protruding element and the second protruding element on an outer surface of the cover, to visually verify rotation of the first connector and the second connector.

Effect

According to embodiments, a rotation axis of a traction member in a knee traction apparatus may be located in front of a knee joint.

Additionally, according to embodiments, a knee traction apparatus may efficiently limit a bending angle of a knee joint, using a stopper.

Moreover, according to embodiments, a knee traction apparatus may reduce manufacturing costs and may facilitate manufacturing, since a connection member is located adjacent to a knee joint.

Furthermore, according to embodiments, a knee traction apparatus may protect cartilages by reducing load applied to a knee joint, may relieve pain of the knee joint, and may induce healing of the knee joint.

In addition, according to embodiments, a knee traction apparatus may support a knee joint so that a user may naturally straighten and bend a knee joint.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
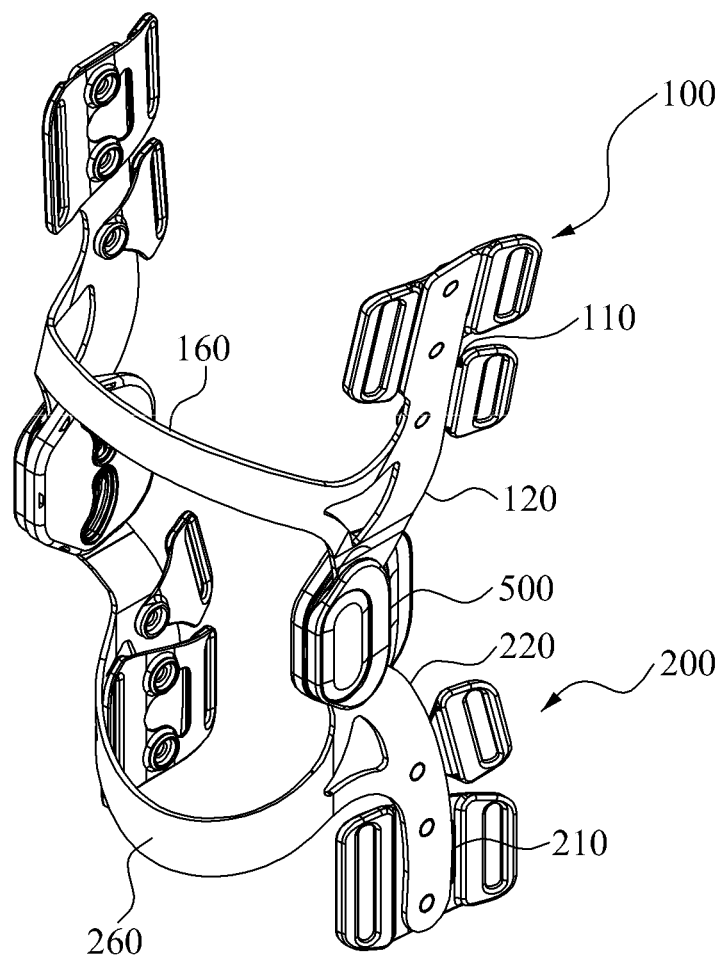
FIG. 1 is a perspective diagram of a knee traction apparatus according to an embodiment.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Figure 2:
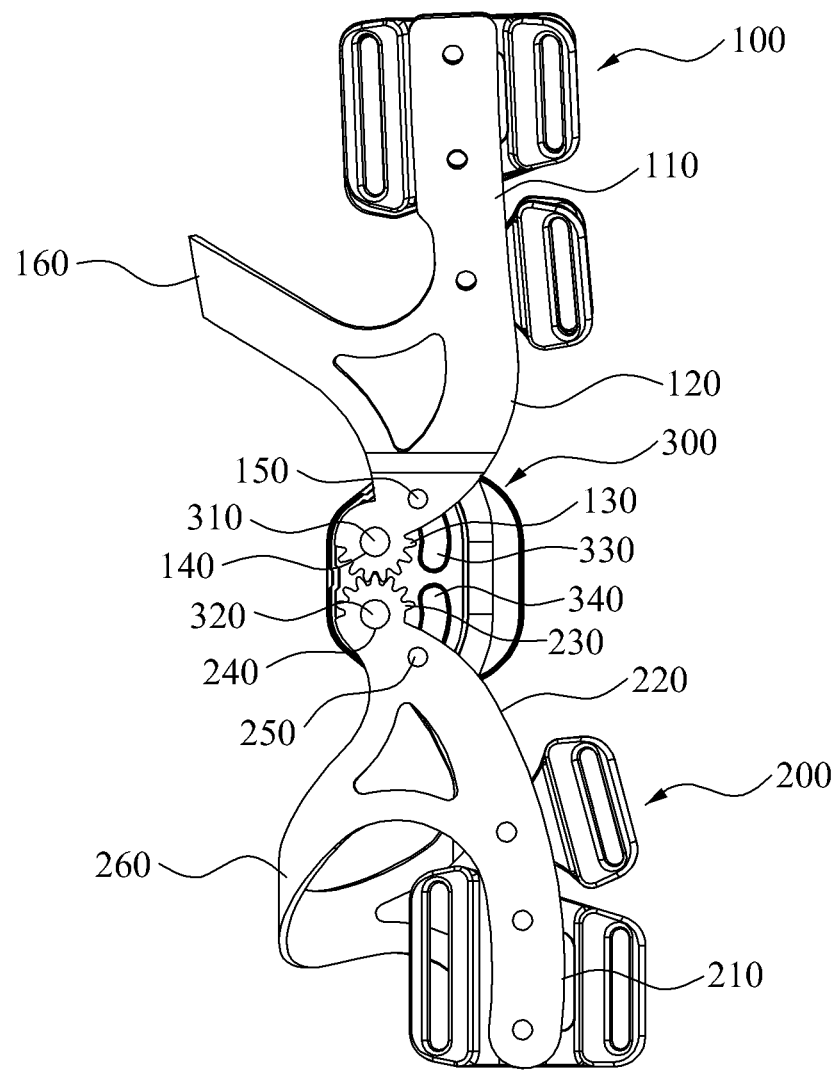
FIG. 2 illustrates an example in which a cover is removed from the knee traction apparatus of FIG. 1 and guide grooves have curved shapes.
Figure 3:
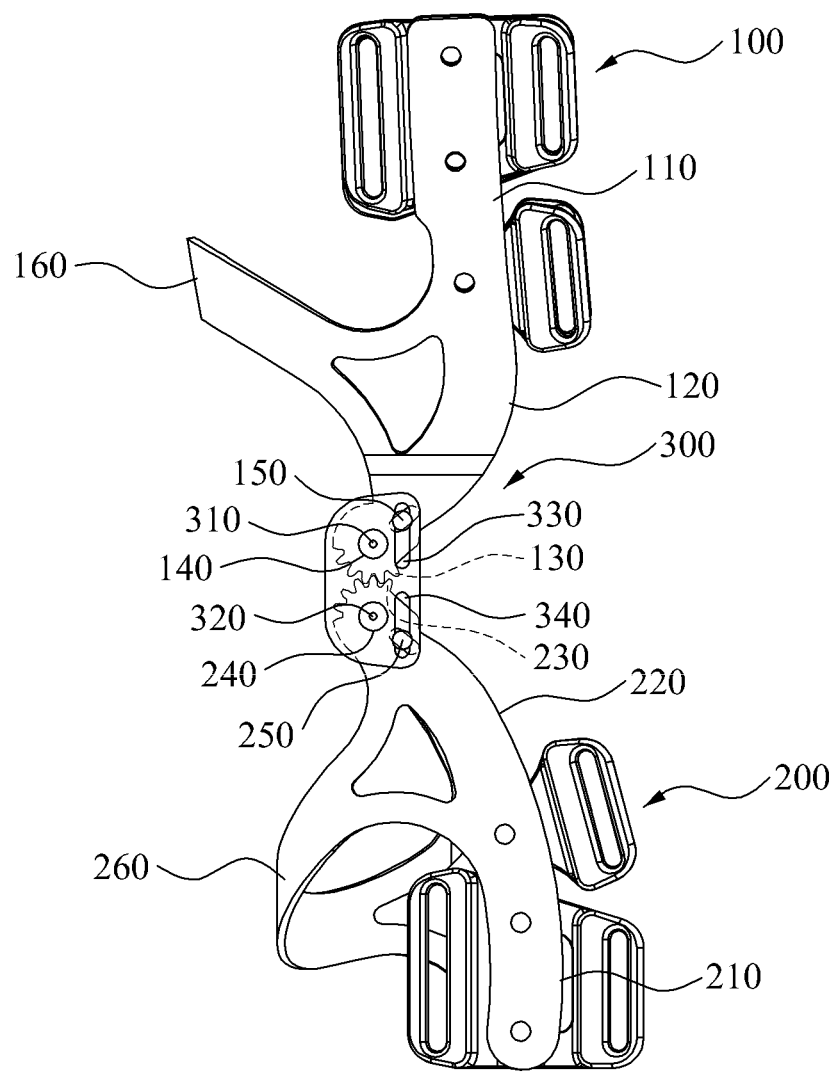
FIG. 3 illustrates an example in which a cover is removed from the knee traction apparatus of FIG. 1 and guide grooves have linear shapes.
Figure 4A:
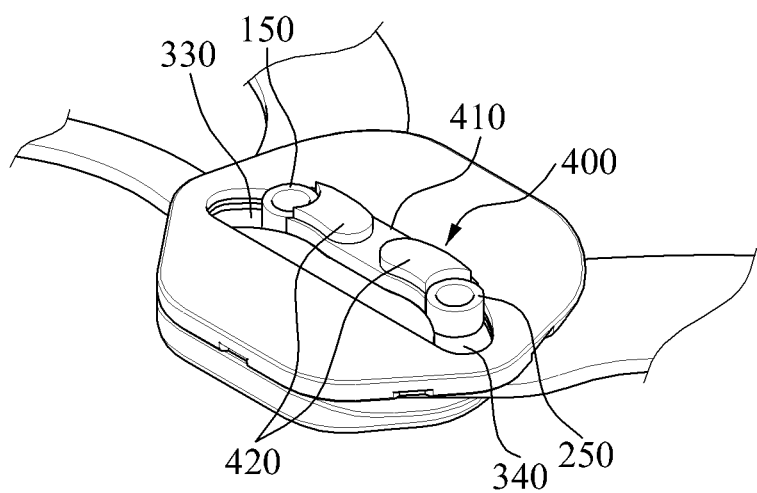
FIGS. 4A through 4C illustrate examples of a stopper installed in the knee traction apparatus of FIG. 1.
Figure 4B:
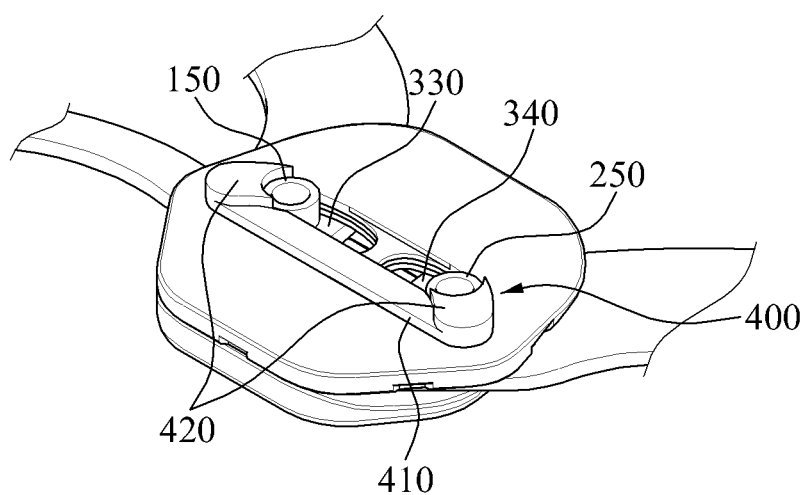
Figure 4C:
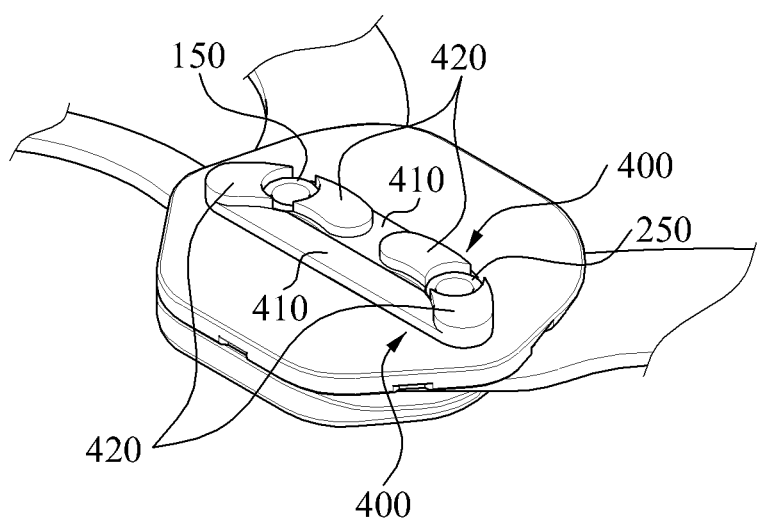
Figure 5:
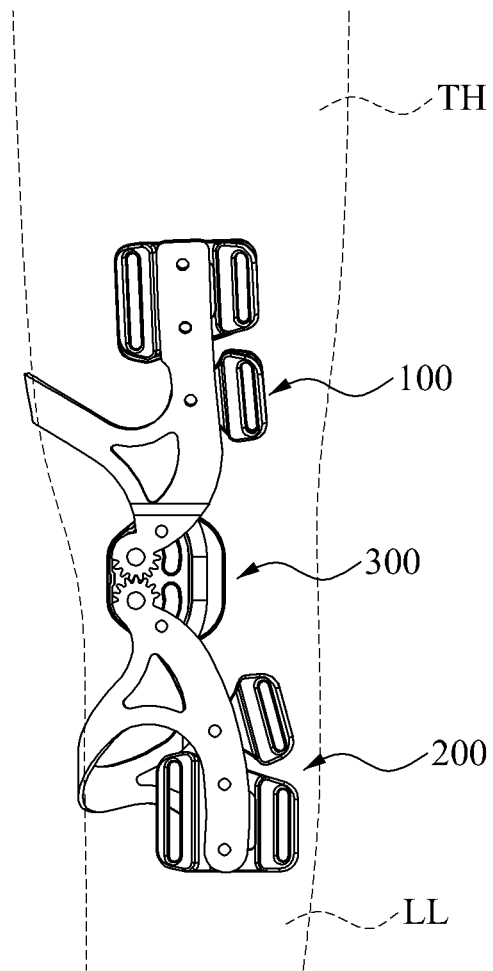
FIG. 5 illustrates an example in which a knee joint of a user wearing the knee traction apparatus of FIG. 1 is straightened.
Figure 6:
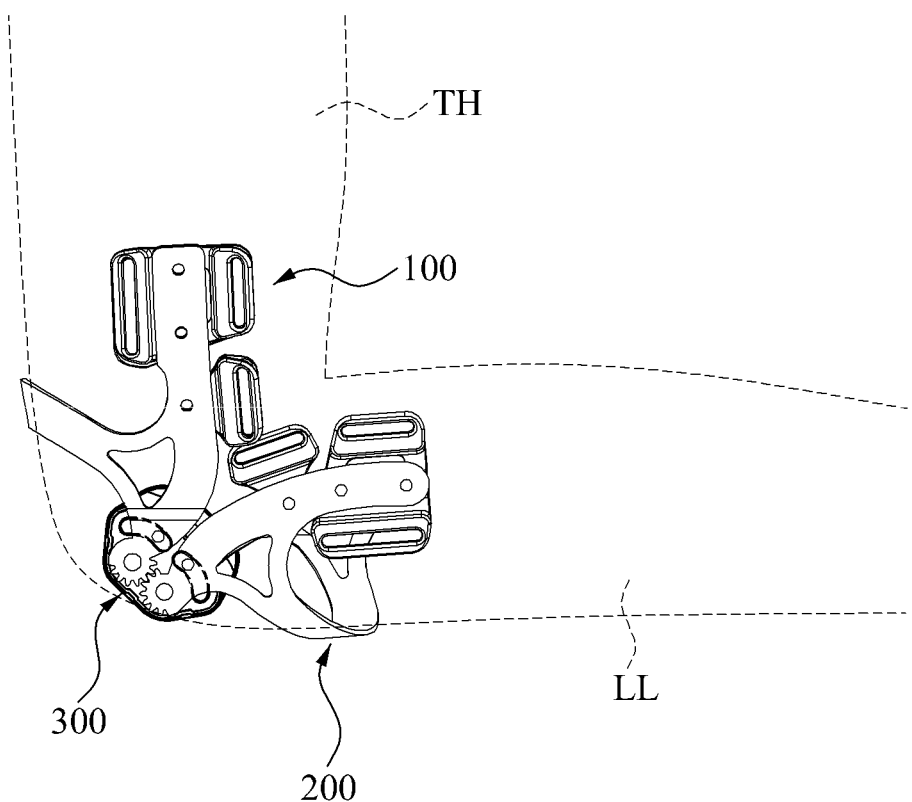
FIG. 6 illustrates an example in which a knee joint of a user wearing the knee traction apparatus of FIG. 1 is bent.

FIG. 1 is a perspective diagram of a knee traction apparatus 10 according to an embodiment, FIG. 2 illustrates an example in which a cover is removed from the knee traction apparatus 10 and guide grooves have curved shapes, and FIG. 3 illustrates an example in which a cover is removed from the knee traction apparatus 10 and guide grooves have linear shapes. FIGS. 4A through 4C illustrate examples of a stopper installed in the knee traction apparatus 10, FIG. 5 illustrates an example in which a knee joint of a user wearing the knee traction apparatus 10 is straightened, and FIG. 6 illustrates an example in which a knee joint of a user wearing the knee traction apparatus 10 is bent.

Referring to FIG. 1, the knee traction apparatus 10 may include an upper frame 100, and a lower frame 200.

The upper frame 100 may be provided to be worn on a thigh region.

The upper frame 100 may include an upper straight member 110, and an upper diagonal member 120. The upper straight member 110 may extend from a side of the thigh region. The upper diagonal member 120 may connect the upper straight member 110 and an upper traction member 130.

Additionally, the lower frame 200 may be provided to be worn on a lower leg region.

The lower frame 200 may include a lower straight member 210, and a lower diagonal member 220. The lower straight member 210 may extend from a side of the lower leg region. The lower diagonal member 220 may connect the lower straight member 210 and a lower traction member 230.

Referring to FIG. 2, the upper traction member 130 and the lower fraction member 230 may be disposed adjacent to a side of a knee joint in an end of the upper frame 100, and an end of the lower frame 200, respectively.

The upper traction member 130 and the lower traction member 230 may be formed integrally with, or separately from the upper frame 100 and the lower frame 200, respectively.

Additionally, the upper traction member 130 and the lower traction member 230 may each have a saw-toothed shape.

A portion of each of the upper traction member 130 and the lower traction member 230 has a saw-toothed shape as shown in FIG. 2, however, a circumferential edge of each of the upper traction member 130 and the lower traction member 230 may have a saw-toothed shape.

Referring to FIG. 3, the upper traction member 130 and the lower fraction member 230 may each have a shape of a quarter of a circle.

For example, when each of the upper traction member 130 and the lower traction member 230 has a quadrant, quadrants may be disposed so that an arc of each of the quadrants may come in contact with each other.

The upper fraction member 130 and the lower traction member 230 may be in contact with each other in front of the knee joint.

Accordingly, a center of rotation of the upper traction member 130 and the lower traction member 230 may be located in front of the knee joint, and the knee joint may be supported so that a user may naturally straighten and bend a knee joint.

Additionally, based on a position in which the upper traction member 130 and the lower traction member 230 are in contact with each other, a shape of each of the upper diagonal member 120 and the lower diagonal member 220 may be changed.

In example, the upper diagonal member 120 and the lower diagonal member 220 may be wound from the upper straight member 110 and the lower straight member 210 toward the upper traction member 130 and the lower traction member 230. In another example, the upper diagonal member 120 and the lower diagonal member 220 may extend from the upper straight member 110 and the lower straight member 210, without a slope.

The upper traction member 130 and the lower traction member 230 formed as described above may rotate in mesh. Additionally, based on a rotation direction of each of the upper traction member 130 and the lower traction member 230, an angle between the upper frame 100 and the lower frame 200 may be changed.

The upper traction member 130 and the lower traction member 230 may be symmetrical to each other, and may rotate in opposite directions.

In an example, when a knee joint is straightened, the upper traction member 130 may rotate counterclockwise, or the lower traction member 230 may rotate clockwise. Accordingly, the angle between the upper frame 100 and the lower frame 200 may increase.

In another example, when the knee joint is bent, the upper traction member 130 may rotate clockwise, or the lower traction member 230 may rotate counterclockwise. Accordingly, the angle between the upper frame 100 and the lower frame 200 may decrease.

The knee traction apparatus 10 may further include a guide member 300 in which a rotation axis of each of the upper traction member 130 and the lower fraction member 230 is located.

The guide member 300 may include a first protrusion 310, a second protrusion 320, a first guide groove 330, and a second guide groove 340.

The first protrusion 310 may be disposed in a center of rotation, that is, a rotation axis of the upper traction member 130, and the second protrusion 320 may be disposed in a center of rotation, that is, a rotation axis of the lower traction member 230.

The upper traction member 130 may include an upper groove 140 into which the first protrusion 310 of the guide member 300 is to be inserted. The lower traction member 230 may include a lower groove 240 into which the second protrusion 320 of the guide member 300 to be is inserted.

The first protrusion 310, the second protrusion 320, the upper groove 140, and the lower groove 240 may be located so that the upper traction member 130 and the lower traction member 230 may rotate in mesh.

Additionally, the upper traction member 130 and the lower traction member 230 may be in contact with each other in front of the knee joint and accordingly, the first protrusion 310 and the second protrusion 320 in the guide member 300 may also be disposed in front of the knee joint.

The first guide groove 330 and the second guide groove 340 may allow the upper traction member 130 and the lower traction member 230 to smoothly rotate. Additionally, the first guide groove 330 and the second guide groove 340 may be located further behind the knee joint than the upper fraction member 130 and the lower traction member 230, respectively.

The first guide groove 330 may guide an upper protruding element 150 inserted into the first guide groove 330. The second guide groove 340 may guide a lower protruding element 250 inserted into the second guide groove 340.

The upper protruding element 150 may protrude inward from the upper frame 100, and the lower protruding element 250 may protrude inward from the lower frame 200.

For example, the upper protruding element 150 and the lower protruding element 250 may move inward from the upper diagonal member 120 and the lower diagonal member 220, respectively.

The first guide groove 330 and the second guide groove 340 may be formed along a moving route of the upper protruding element 150 and a moving route of the lower protruding element 250, respectively. Additionally, the upper protruding element 150 and the lower protruding element 250 may be provided to be inserted into the first guide groove 330 and the second guide groove 340, respectively.

The first guide groove 330 and the second guide groove 340 may be symmetrical to each other, and may each have a curved shape. The upper protruding element 150 and the lower protruding element 250 may also be symmetrical to each other, and may move while drawing curved tracks.

As shown in FIG. 3, the first guide groove 330 and the second guide groove 340 may be symmetrical to each other, and may each have a linear shape. Additionally, the upper protruding element 150 and the lower protruding element 250 may be symmetrical to each other, and may move while drawing linear tracks within the first guide groove 330 and the second guide groove 340.

The upper protruding element 150 and the lower protruding element 250 may move outward, in addition to inward, from the upper diagonal member 120 and the lower diagonal member 220, respectively.

In an example, when a knee joint is straightened, the angle between the upper frame 100 and the lower frame 200 may increase, and the upper traction member 130 and the lower traction member 230 may rotate based on an increase in the angle. Accordingly, the upper protruding element 150 and the lower protruding element 250 may be guided toward the other end of the upper frame 100 and the other end of the lower frame 200 within the first guide groove 330 and the second guide groove 340, respectively, and a distance between the upper protruding element 150 and the lower protruding element 250 may increase.

In another example, when the knee joint is bent, the angle between the upper frame 100 and the lower frame 200 may decrease, and the upper traction member 130 and the lower traction member 230 may rotate based on a decrease in the angle. Accordingly, the upper protruding element 150 and the lower protruding element 250 may be guided toward the end of the upper frame 100 and the end of the lower frame 200 within the first guide groove 330 and the second guide groove 340, respectively, and the distance between the upper protruding element 150 and the lower protruding element 250 may decrease.

By the guide member 300 formed as described above, the upper traction member 130 and the lower traction member 230 may smoothly rotate, and the knee joint may be naturally straightened and bent.

Referring to FIGS. 4A through 4C, a stopper 400 may be installed in the first guide groove 330 and the second guide groove 340.

The stopper 400 may include a straight portion 410, and pivoting portions 420 disposed in both ends of the straight portion 410.

The straight portion 410 may be located outside the first guide groove 330 and the second guide groove 340. The pivoting portions 420 may be located in the first guide groove 330 and the second guide groove 340, respectively.

The pivoting portions 420 may be pivotable with respect to the straight portion 410. Accordingly, an angle between the straight portion 410 and the pivoting portions 420 may be adjusted.

In an example, when a short straight portion 410 is included in a stopper 400 as shown in FIG. 4A, pivoting portions 420 may be installed close to each other in the first guide groove 330 and the second guide groove 340. Accordingly, by preventing the upper protruding element 150 and the lower protruding element 250 from moving close to each other, it is possible to prevent a further reduction in the angle between the upper frame 100 and the lower frame 200.

In another example, when a long straight portion 410 is included in a stopper 400 as shown in FIG. 4B, pivoting portions 420 may be installed far away from each other in the first guide groove 330 and the second guide groove 340. Accordingly, by preventing the upper protruding element 150 and the lower protruding element 250 from moving far away from each other, it is possible to prevent a further increase in the angle between the upper frame 100 and the lower frame 200.

The stoppers 400 of FIGS. 4A and 4B having different shapes may be individually installed, however, there is no limitation thereto. For example, stoppers 400 with different shapes may be installed together as shown in FIG. 4C. For example, the upper protruding element 150 and the lower protruding element 250 may be fixed by the stopper 400 within the first guide groove 330 and the second guide groove 340, and accordingly may not move in a direction.

Additionally, to facilitate installation of the stopper 400, the guide member 300 may have a hollow portion in a position in which the stopper 400 is to be installed.

The stopper 400 may limit movement of the upper protruding element 150 and the lower protruding element 250 within the first guide groove 330 and the second guide groove 340, may limit rotation of the upper traction member 130 and the lower traction member 230, and may fix the angle between the upper frame 100 and the lower frame 200.

The upper frame 100 and the lower frame 200 may include an upper connection member 160 and a lower connection member 260, respectively.

The upper connection member 160 may connect upper straight members 110 extending from both ends of the thigh region. The lower connection member 260 may connect lower straight members 210 extending from both ends of the lower leg region.

The upper connection member 160 may be formed between the other end of the upper frame 100 and the upper traction member 130. The lower connection member 260 may be formed between the other end of the lower frame 200 and the lower traction member 230.

For example, the upper connection member 160 and the lower connection member 260 may be located adjacent to a knee joint, and may be configured to enclose the knee joint.

The upper connection member 160 may be curved to cover an upper side of the knee joint, and the lower connection member 260 may be curved to cover a lower side of the knee joint.

Due to the upper connection member 160 and the lower connection member 260 disposed adjacent to the knee joint, a material with relatively low strength may be used to manufacture the upper frame 100 and the lower frame 200. Accordingly, it is possible to reduce manufacturing costs.

In other words, when the upper connection member 160 is formed in a middle portion of the upper straight member 110 of the upper frame 100, and when the lower connection member 260 is formed in a middle portion of the lower straight member 210 of the lower frame 200, the upper frame 100 and the lower frame 200 may be formed of a material or elastic material with low strength, compared to when the upper connection member 160 and the lower connection member 260 are formed in the other end of the upper frame 100 and the other end of the lower frame 200, respectively.

When the upper straight member 110 and the lower straight member 210 are formed of elastic materials in the upper frame 100 and the lower frame 200, respectively, users may use the knee traction apparatus 10, regardless of a size of each of a thigh region and a lower leg region of each of the users, and a wearing sensation may be enhanced.

Additionally, the knee traction apparatus 10 may include a cover 500 to protect the upper traction member 130, the lower traction member 230, and the guide member 300.

The cover 500 may prevent the upper traction member 130, the lower traction member 230, and the guide member 300 from being damaged by outside exposure and accordingly, a life of the knee traction apparatus 10 may be extended.

Furthermore, the cover 500 may be detachably provided and accordingly, it is possible to facilitate maintenance of the upper traction member 130, the lower traction member 230, and the guide member 300.

The knee traction apparatus 10 configured as described above may be worn on a knee, and may operate as follows.

In an example, when a knee joint in a bent state is straightened, as shown in FIG. 5, the upper traction member 130 may rotate counterclockwise about the first protrusion 310 of the guide member 300, or the lower fraction member 230 may rotate clockwise about the second protrusion 320 of the guide member 300.

In this example, the first protrusion 310 may be inserted into the upper groove 140, and the second protrusion 320 may be inserted into the lower groove 240.

Accordingly, the upper protruding element 150 in the upper frame 100 may move toward the other end of the upper frame 100 along the first guide groove 330 of the guide member 300, or the lower protruding element 250 in the lower frame 200 may move toward the other end of the lower frame 200 along the second guide groove 340 of the guide member 300.

The upper traction member 130 and the lower traction member 230 may rotate so that the angle between the upper frame 100 and the lower frame 200 may increase.

Additionally, when rotation of the upper traction member 130 and the lower traction member 230 is terminated, the stopper 400, although not shown in FIG. 5, may be installed in the guide member 300 to fix a state in which the upper traction member 130 and the lower traction member 230 do not rotate.

In another example, when a knee joint in a straightened state is bent, as shown in FIG. 6, the upper fraction member 130 may rotate clockwise about the first protrusion 310 of the guide member 300, or the lower traction member 230 may rotate counterclockwise about the second protrusion 320 of the guide member 300.

Accordingly, the upper protruding element 150 in the upper frame 100 may move toward the end of the upper frame 100 along the first guide groove 330 of the guide member 300, or the lower protruding element 250 in the lower frame 200 may move toward the end of the lower frame 200 along the second guide groove 340 of the guide member 300.

The upper traction member 130 and the lower traction member 230 may rotate so that the angle between the upper frame 100 and the lower frame 200 may be changed.

Additionally, when the rotation of the upper traction member 130 and the lower traction member 230 is terminated, the stopper 400, although not shown in FIG. 6, may be installed in the guide member 300 to fix a state in which the upper traction member 130 and the lower traction member 230 do not rotate.

As described above, a knee traction apparatus according to an embodiment may allow a rotation axis of each of an upper traction member and a lower traction member to be located in front of a knee joint, and may efficiently limit a bending angle of the knee joint, using a stopper. Additionally, an upper connection member and a lower connection member may be located adjacent to the knee joint and accordingly, it is possible to reduce manufacturing costs and to facilitate manufacturing. Furthermore, the knee traction apparatus may protect cartilages by reducing load applied to the knee joint, may induce healing of the knee joint by relieving pain of the knee joint, and may support the knee joint so that a user may naturally straighten and bend the knee joint.

Figure 7:
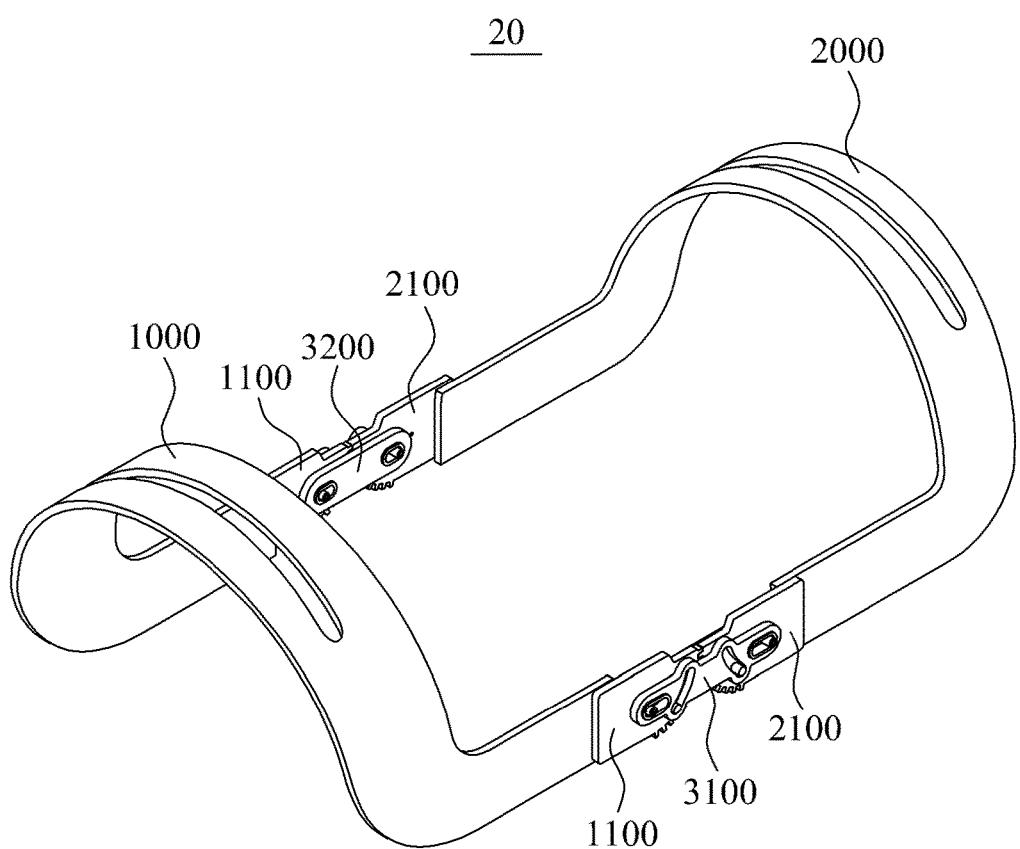
FIG. 7 is a perspective diagram illustrating an internal structure of a knee traction apparatus according to an embodiment.
Figure 8:
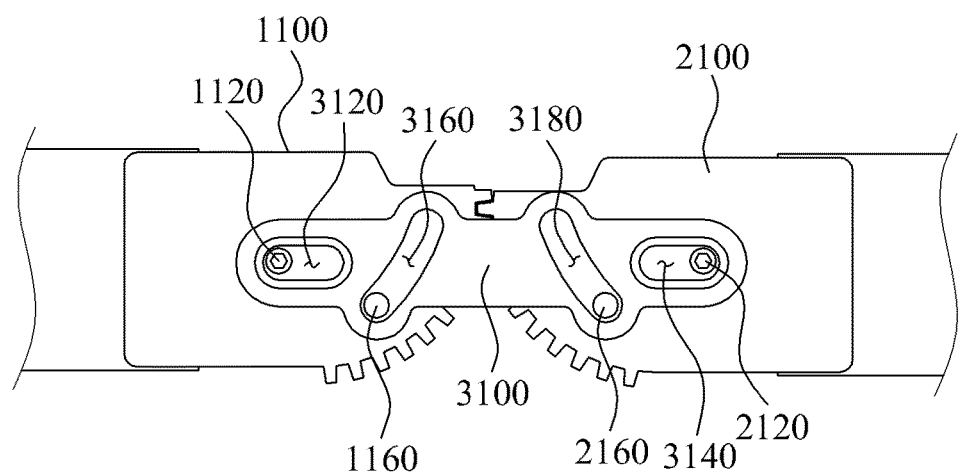
FIG. 8 illustrates an exterior of connectors of the knee traction apparatus of FIG. 7.
Figure 9:
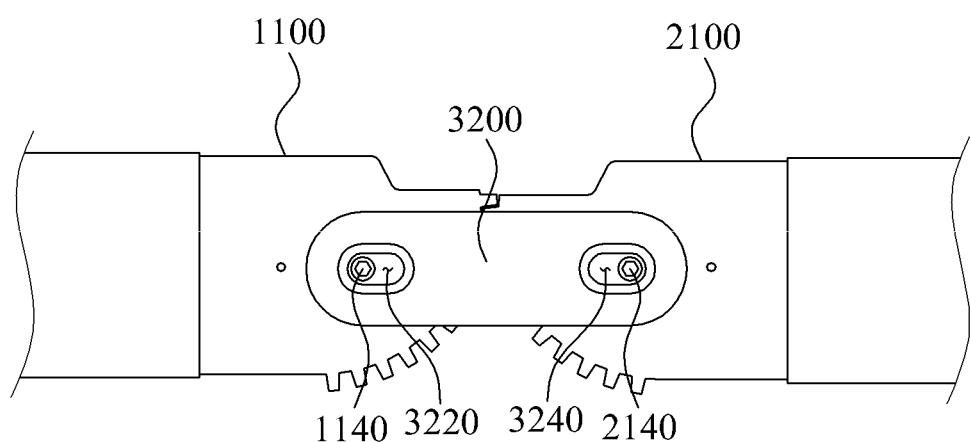
FIG. 9 illustrates an interior of connectors of the knee traction apparatus of FIG. 7.
Figure 10:
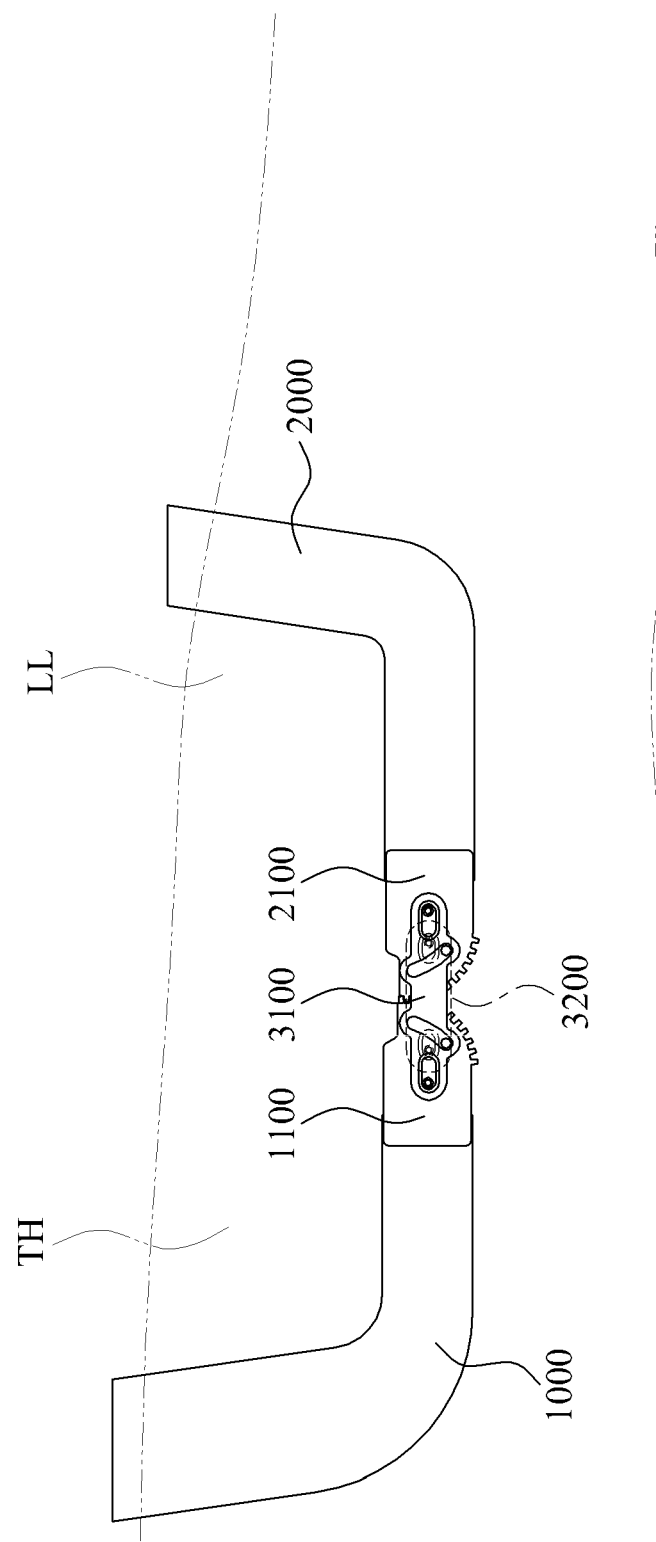
FIG. 10 illustrates an example in which a knee of a user wearing the knee traction apparatus of FIG. 7 is straightened.
Figure 11:
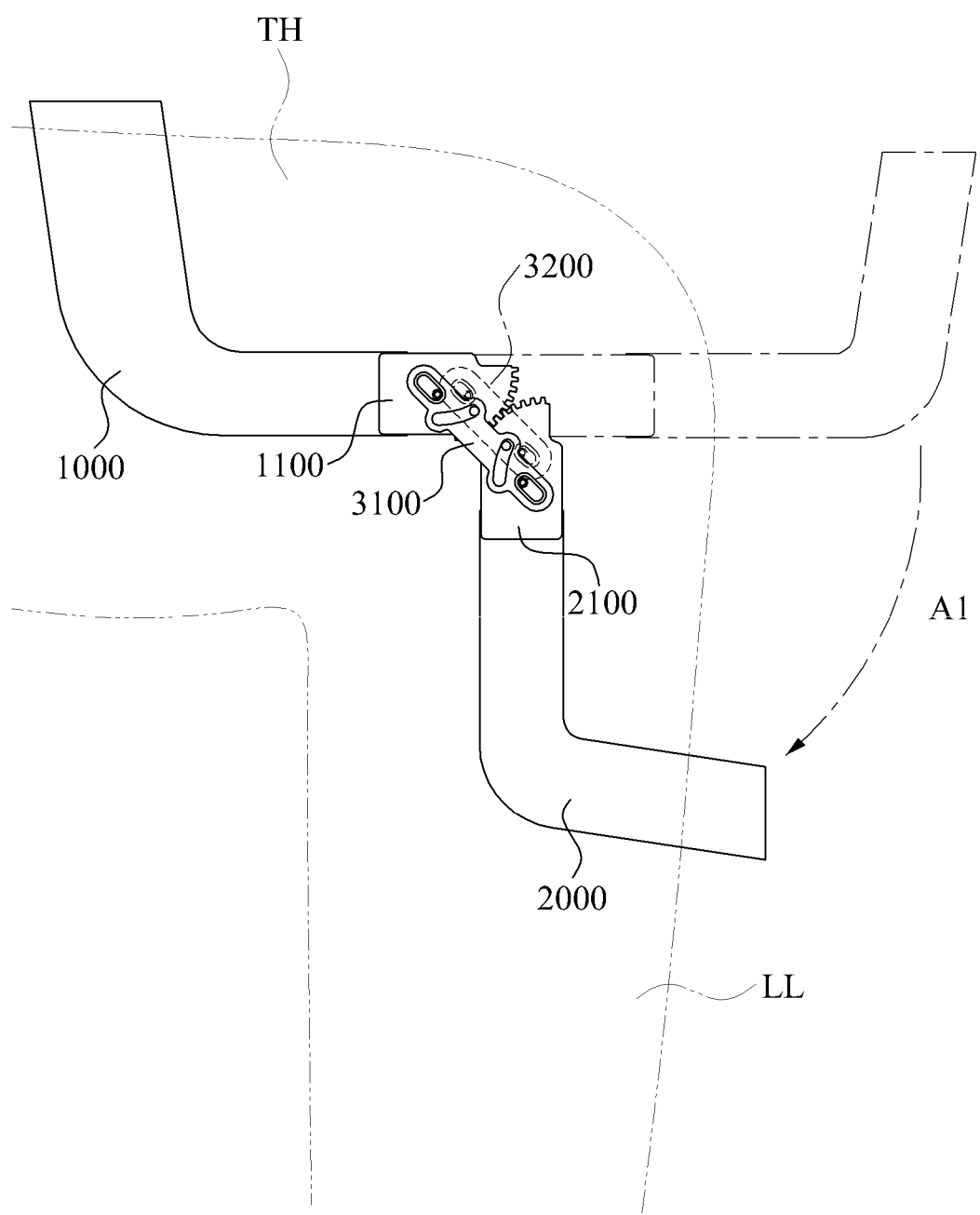
FIG. 11 illustrates an example in which a knee of a user wearing the knee traction apparatus of FIG. 7 is bent.
Figure 12:
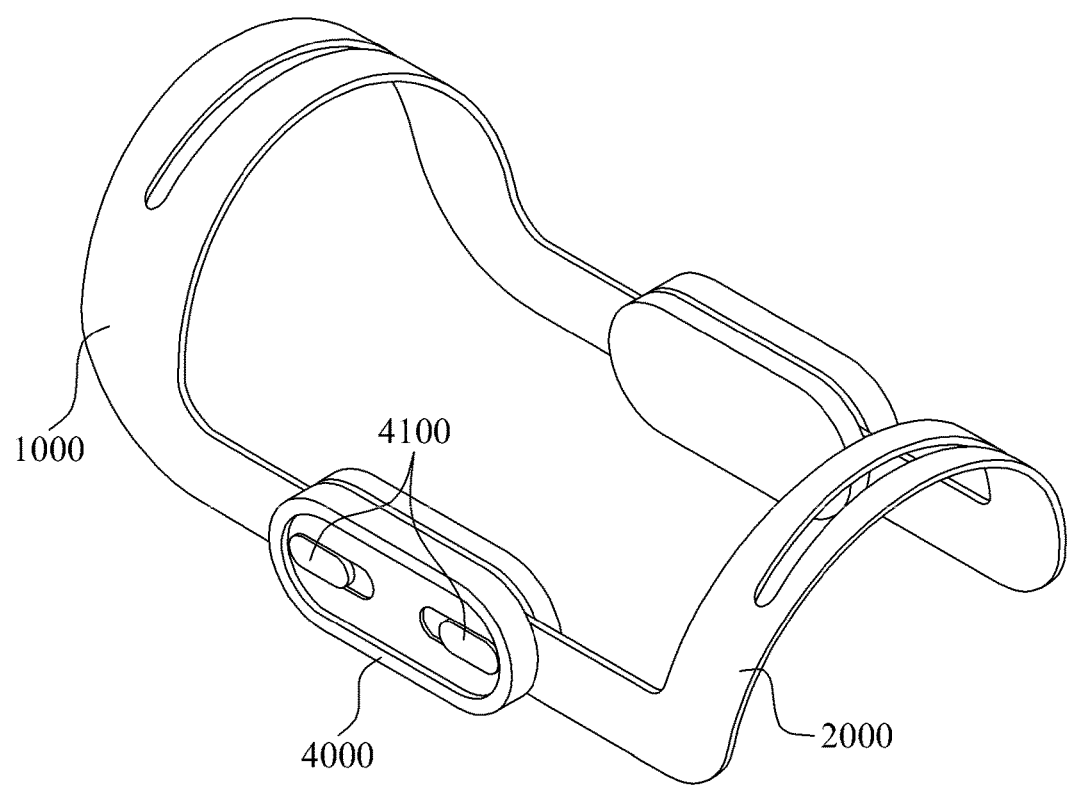
FIG. 12 illustrates the knee traction apparatus of FIG. 7 covered by a cover.
Figure 13:
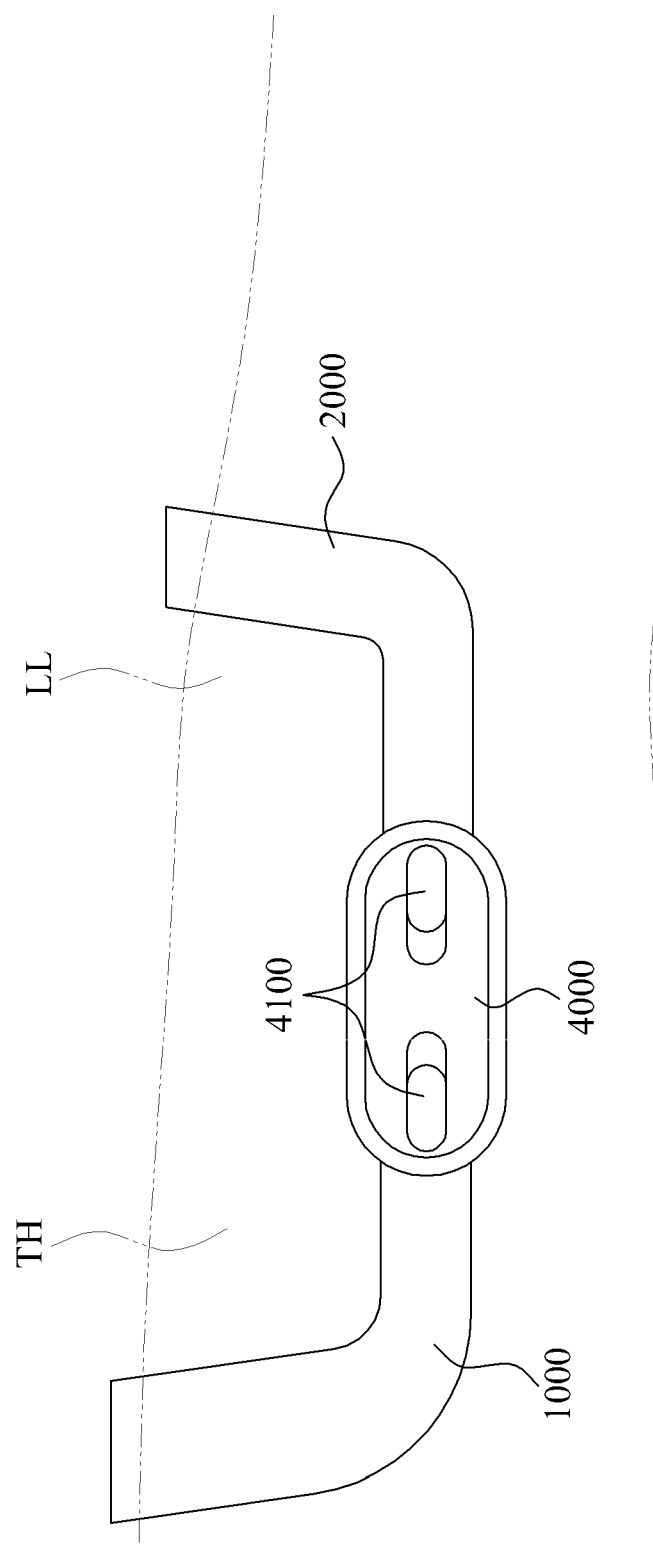
FIG. 13 illustrates an example in which a knee is straightened while wearing the knee traction apparatus of FIG. 7 covered by the cover.
Figure 14:
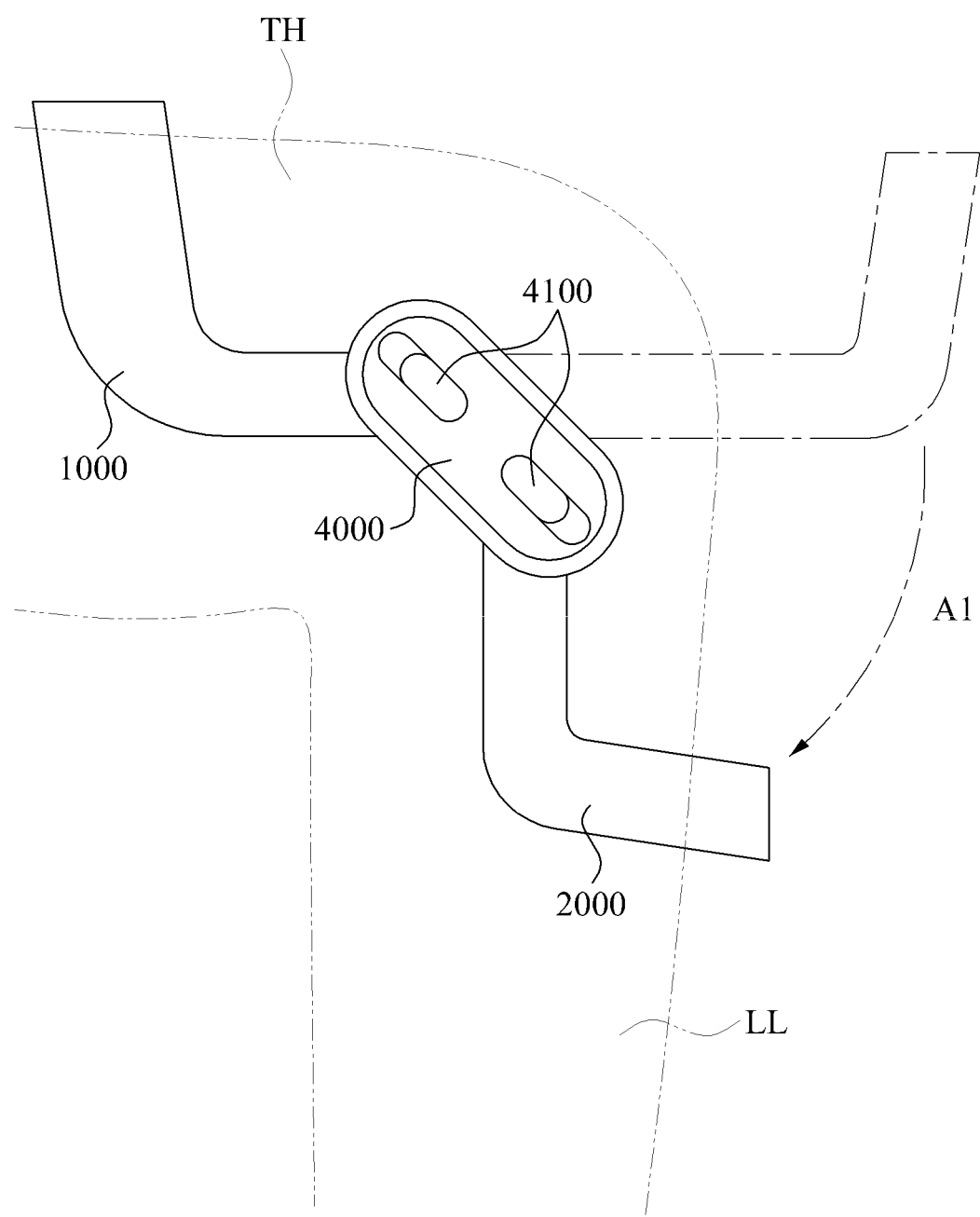
FIG. 14 illustrates an example in which a knee is bent while wearing the knee traction apparatus of FIG. 7 covered by the cover.

FIG. 7 is a perspective diagram illustrating an internal structure of a knee traction apparatus 20 according to an embodiment, FIG. 8 illustrates an exterior of connectors of the knee traction apparatus 20, and FIG. 9 illustrates an interior of connectors of the knee traction apparatus 20. FIG. 10 illustrates an example in which a knee of a user wearing the knee traction apparatus 20 is straightened, and FIG. 11 illustrates an example in which a knee of a user wearing the knee fraction apparatus 20 is bent. FIG. 12 illustrates the knee traction apparatus 20 covered by a cover 4000, FIG. 13 illustrates an example in which a knee is straightened while wearing the knee traction apparatus 20 covered by the cover 4000, and FIG. 14 illustrates an example in which a knee is bent while wearing the knee traction apparatus 20 covered by the cover 4000.

Referring to FIGS. 7 through 11, the knee traction apparatus 20 may include an upper frame 1000, a lower frame 2000, and a guide member 3000.

The upper frame 1000 may be provided to be worn on a thigh region of a user. For example, the upper frame 1000 may be worn on an anterior surface of the thigh region.

A shape of the upper frame 1000 may not be limited to FIG. 8, and the upper frame 1000 may have various shapes. For example, the upper frame 1000 may have a structure enabling a size of the upper frame 1000 to be adjusted, because thigh regions of users may have different sizes.

Additionally, the upper frame 1000 may include a pad to enable a user to feel comfortable about wearing the knee traction apparatus 20. The pad may be attached or detached by a Velcro to or from the upper frame 1000.

The upper frame 1000 may include a first connector 1100 disposed in an end of the upper frame 1000.

The first connector 1100 may be formed integrally with, or separately from the upper frame 1000.

An end portion of the first connector 1100 may have an oval shape, and may have a saw-toothed edge. A second connector 2100 of the lower frame 2000 that will be described later may have the same structure as the first connector 1100 and accordingly, the first connector 1100 and the second connector 2100 may rotate in mesh.

The lower frame 2000 may be disposed to come in contact with the end of the upper frame 1000.

The lower frame 2000 may be provided to be worn on a lower leg region. For example, to support the lower leg region, the lower frame 2000 may be worn on an anterior surface of the lower leg region.

The lower frame 2000 may also have various shapes, similarly to the upper frame 1000. To enable a user to feel comfortable about wearing the knee traction apparatus 20, the lower frame 2000 may include a pad that is detachably coupled to the lower frame 2000.

The lower frame 2000 may include the second connector 2100 disposed in an end of the lower frame 2000.

An end portion of the second connector 2100 may have an oval shape, and may have a saw-toothed edge. Accordingly, the first connector 1100 and the second connector 2100 may rotate in mesh.

Due to an oval-shaped contact area between the first connector 1100 and the second connector 2100, the first connector 1100 and the second connector 2100 may rotate in contact with each other while drawing oval tracks. In other words, while the first connector 1100 and the second connector 2100 rotate, a distance between the upper frame 1000 and the lower frame 2000 may increase or decrease.

In an example, when a knee is straightened, a major axis of the oval track of the first connector 1100 and a major axis of the oval track of the second connector 2100 may be aligned, and accordingly the distance between the upper frame 1000 and the lower frame 2000 may have a maximum value. In this example, the upper frame 1000 and the lower frame 2000 may support a thigh region TH and a lower leg region LL, respectively, and a femur and cartilage of a knee joint may be spaced apart from each other. Accordingly, the knee joint may be protected against load applied when coming in contact with a ground.

In another example, when the knee is bent, the major axis of the first connector 1100 and a minor axis of the second connector 2100 may be generally disposed in parallel with each other and accordingly, the distance between the upper frame 1000 and the lower frame 2000 may decrease.

Additionally, the saw-toothed edge of each of the first connector 1100 and the second connector 2100 may enable the first connector 1100 and the second connector 2100 to be more securely engaged with each other and accordingly, rotation of the first connector 1100 and the second connector 2100 may be ensured.

The end portion of the first connector 1100 may have the saw-toothed edge in the knee traction apparatus 20, however, the knee traction apparatus 20 may have all structures enabling the first connector 1100 and the second connector 2100 to rotate in contact with each other. For example, the end portion of each of the first connector 1100 and the second connector 2100 may have a curved shape.

In the first connector 1100 and the second connector 2100, a plurality of protruding elements may be formed. For example, the first connector 1100 may include a first protruding element 1120 protruding outward from a focal point of the first connector 1100, a third protruding element 1140 protruding inward from a central point of the first connector 1100, and a fifth protruding element 1160 protruding outward from the first connector 1100.

Additionally, the second connector 2100 may include a second protruding element 2120 protruding outward from a focal point of the second connector 2100, a fourth protruding element 2140 protruding inward from a central point of the second connector 2100, and a sixth protruding element 2160 protruding outward from the second connector 2100.

The first protruding element 1120 to the sixth protruding element 2160 may be inserted into a first groove 3120 to a sixth groove 3180 of the guide member 3000 that will be described below.

The guide member 3000 may be disposed in a side of each of the first connector 1100 and the second connector 2100, and may stably guide rotation of the first connector 1100 and the second connector 2100.

The guide member 3000 may include an outer guide member 3100, and an inner guide member 3200. The outer guide member 3100 may be disposed outside the first connector 1100 and the second connector 2100, and may extend from the first connector 1100 to the second connector 2100. The inner guide member 3200 may be disposed inside the first connector 1100 and the second connector 2100, and may extend from the first connector 1100 to the second connector 2100.

The outer guide member 3100 may connect the first protruding element 1120 and the second protruding element 2120.

The outer guide member 3100 may include the first groove 3120 into which the first protruding element 1120 is inserted, and a second groove 3140 into which the second protruding element 2120 is inserted. The first groove 3120 may be disposed in a side of the first connector 1100, and the second groove 3140 may be disposed in a side of the second connector 2100. The first groove 3120 and the second groove 3140 may be symmetrical to each other in the outer guide member 3100.

The first groove 3120 and the second groove 3140 may be aligned in the outer guide member 3100, and may each have a linear shape. Accordingly, the first protruding element 1120 and the second protruding element 2120 inserted into the first groove 3120 and the second groove 3140 may move linearly in the first groove 3120 and the second groove 3140, while the first connector 1100 and the second connector 2100 rotate, respectively.

By engaging the first protruding element 1120 and the second protruding element 2120 with the first groove 3120 and the second groove 3140, rotation of the first connector 1100 and the second connector 2100 may be supported, and the first protruding element 1120 and the second protruding element 2120 may move in the first groove 3120 and the second groove 3140. Thus, the first connector 1100 and the second connector 2100 may smoothly rotate.

Additionally, the inner guide member 3200 may connect the third protruding element 1140 and the fourth protruding element 2140.

The inner guide member 3200 may include a third groove 3220 into which the third protruding element 1140 is inserted, and a fourth groove 3240 into which the fourth protruding element 2140 is inserted, and may connect the third protruding element 1140 and the fourth protruding element 2140.

The third groove 3220 and the fourth groove 3240 may be aligned in the inner guide member 3200, and may each have a linear shape. Accordingly, the third protruding element 1140 and the fourth protruding element 2140 inserted into the third groove 3220 and the fourth groove 3240 may linearly move in the third groove 3220 and the fourth groove 3240, respectively, while the first connector 1100 and the second connector 2100 rotate, respectively.

By engaging the third protruding element 1140 and the fourth protruding element 2140 with the third groove 3220 and the fourth groove 3240, the rotation of the first connector 1100 and the second connector 2100 may be supported in the inner guide member 3200 as well as in the outer guide member 3100. Additionally, the third protruding element 1140 and the fourth protruding element 2140 may move in the third groove 3220 and the fourth groove 3240. Thus, the first connector 1100 and the second connector 2100 may smoothly rotate.

Additionally, the outer guide member 3100 may include a fifth groove 3160 into which the fifth protruding element 1160 is inserted, and a sixth groove 3180 into which the sixth protruding element 2160 is inserted. Each of the fifth groove 3160 and the sixth groove 3180 may have a curved shape.

For example, the curved shape of each of the fifth groove 3160 and the sixth groove 3180 may have the same curvature as a track drawn while the first connector 1100 and the second connector 2100 rotate.

Accordingly, the fifth protruding element 1160 and the sixth protruding element 2160 inserted into the fifth groove 3160 and the sixth groove 3180 may curvilinearly move along the fifth groove 3160 and the sixth groove 3180 while the first connector 1100 and the second connector 2100 rotate.

The structure of the knee traction apparatus 20 has been described above, and an operation of the knee traction apparatus 20 will be described hereinafter.

Hereinafter, an example in which a knee of a user wearing the knee traction apparatus 20 is straightened is described with reference to FIG. 10.

For example, the knee may be straightened while the lower frame 2000 rotates about the upper frame 1000.

In this example, the second connector 2100 may rotate in mesh with the first connector 1100. The second connector 2100 may rotate toward the major axis of the first connector 1100 while drawing an oval track and accordingly, the distance between the upper frame 1000 and the lower frame 2000 may have the maximum value.

The second protruding element 2120 of the second connector 2100 may move to the right through the second groove 3140 of the outer guide member 3100, and the fourth protruding element 2140 of the second connector 2100 may move to the right through the fourth groove 3240 of the inner guide member 3200. Additionally, the sixth protruding element 2160 of the second connector 2100 may move downward along the oval track through the sixth groove 3180 of the outer guide member 3100.

As described above, since the distance between the upper frame 1000 worn on the thigh region and the lower frame 2000 worn on the lower leg region increases, a femur and cartilage of a knee joint may be spaced apart from each other when the knee is straightened. Thus, it is possible to protect the cartilage by reducing pressure caused by load.

Additionally, an example in which a knee of a user wearing the knee traction apparatus 20 is bent will be described with reference to FIG. 11.

For example, the knee may be bent while the lower frame 2000 rotates about the upper frame 1000, as indicated by an arrow A1.

In this example, the second connector 2100 may rotate clockwise in mesh with the first connector 1100. The second connector 2100 may move toward a minor axis of the first connector 1100 while rotating and accordingly, the distance between the upper frame 1000 and the lower frame 2000 may be reduced.

The second protruding element 2120 of the second connector 2100 may move to the left through the second groove 3140 of the outer guide member 3100, and the fourth protruding element 2140 of the second connector 2100 may move to the left through the fourth groove 3240 of the inner guide member 3200. Additionally, the sixth protruding element 2160 of the second connector 2100 may move upward along the oval track through the sixth groove 3180 of the outer guide member 3100.

As described above, since the distance between the upper frame 1000 worn on the thigh region and the lower frame 2000 worn on the lower leg region gradually decreases, the user may naturally bend the knee.

For example, due to softening of cartilages, cartilages may not properly function to support a weight of a body and mitigate an impact. In this example, pain may be caused every time a knee is bent. Accordingly, by wearing the knee traction apparatus 20, it is possible to relieve the pain.

The knee traction apparatus 20 may be advantageous in bending and straightening of the knee. For example, when a patient with arthritis uses the knee traction apparatus 20, pain may be relieved, and the knee traction apparatus 20 may be a help to treat the arthritis.

Referring to FIG. 12, the cover 4000 may be provided in the knee traction apparatus 20, to protect the first connector 1100, the second connector 2100, and the guide member 3000.

The cover 4000 may cover the first connector 1100, the second connector 2100, and the guide member 3000.

Additionally, the cover 4000 may include a movement element 4100 to visually verify rotation of the first connector 1100 and the second connector 2100. The movement element 4100 may be connected to the first protruding element 1120 and the second protruding element 2120, and may move along with the first protruding element 1120 and the second protruding element 2120.

Furthermore, when a luminous material is included in the movement element 4100, the movement element 4100 may stick out even in a dark place, which may protect a user.

Hereinafter, an example in which the movement element 4100 moves when a knee is straightened or bent is described with reference to FIGS. 13 and 14.

Because the movement element 4100 may be connected to the first protruding element 1120 and the second protruding element 2120 outside the cover 400, the movement element 4100 may move in a movement direction of each of the first protruding element 1120 and the second protruding element 2120.

For example, when a knee is straightened, the first protruding element 1120 may move linearly to the left, and the second protruding element 2120 may move linearly to the right. In another example, when the knee is bent, the first protruding element 1120 may move linearly to the right, and the second protruding element 2120 may move linearly to the left. The first protruding element 1120 and the second protruding element 2120 may move toward a major axis or a minor axis of each of the first connector 1100 and the second connector 2100.

As described above, the cover 4000 may further include the movement element 4100 and accordingly, movement of the first protruding element 1120 and the second protruding element 2120 as well as rotation of the first connector 1100 and the second connector 2100 may be visually verified.

The above-described knee traction apparatus 20 may be used as a joint supporter for a joint moving similarly to a knee, for example, an elbow, and the like, in addition to a knee.

For example, when a joint supporter is worn on an elbow, an upper supporter and a lower supporter may be worn on an upper arm region and a lower arm region, respectively. Additionally, the upper supporter may include a first connector disposed in an end portion of the upper supporter, and the lower supporter may include a second connector disposed in an end portion of the lower supporter. The upper supporter and the lower supporter may have sizes and dimensions to stably wrap an arm.

In this example, the first connector and the second connector may each have an oval shape, and an end portion of each of the first connector and the second connector may have a saw-toothed shape. Accordingly, the first connector and the second connector may rotate in mesh while drawing oval tracks.

Additionally, a link portion may be disposed inside and outside the first connector and the second connector, to support rotation of the first connector and the second connector. The link portion may include an inner link portion installed inside the first connector and the second connector, and an outer link portion installed outside the first connector and the second connector.

Accordingly, the upper arm region and the lower arm region may be stably straightened and bent, without damaging an elbow joint.

As described above, when a knee is straightened, a knee traction apparatus according to an embodiment may support a thigh region and a lower leg region, and a femur and cartilage of a knee joint may be spaced apart from each other and accordingly, it is possible to reduce load applied to the knee when coming in contact with a ground. Thus, it is possible to protect the cartilage and to relieve pain of the knee joint. In addition, the knee traction apparatus may be used as a joint supporter applicable to joints other than the knee joint.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A knee traction apparatus, comprising:
   an upper frame provided to be worn on a thigh region, wherein the upper frame comprises:
   an upper straight member configured to extend from a side of the thigh region, wherein the upper straight member has a proximal end and a distal end, wherein the upper straight member proximal end is positioned above the upper straight member distal end,
   an upper diagonal member having a proximal end and a distal end, wherein the upper diagonal member is positioned beneath the upper straight member, wherein the upper diagonal member extends from the proximal end to the distal end in a diagonal manner in relation to an extension direction of the upper straight member,
   an upper traction member positioned at the distal end of the upper diagonal member, wherein the upper traction member is positioned beneath the upper straight member and beneath the upper diagonal member; and
   a lower frame provided to be worn on a lower leg region, wherein the lower frame comprises:
   a lower straight member configured to extend from a side of the lower leg region, wherein the lower straight member has a proximal end and a distal end, wherein the lower straight member distal end is positioned above the lower straight member proximal end,
   a lower diagonal member having a proximal end and a distal end, wherein the lower diagonal member is positioned above the lower straight member, wherein the lower diagonal member extends from the proximal end to the distal end in a diagonal manner in relation to an extension direction of the lower straight member,
   a lower traction member positioned at the distal end of the lower diagonal member, wherein the lower traction member is positioned above the lower straight member and above the lower diagonal member,
   wherein the lower traction member is positioned with the upper traction member such that the lower traction member is capable of rotation in mesh with the upper traction member,
   wherein the upper traction member and the lower traction member are configured to be in contact with each other in front of a knee joint,
   wherein the upper traction member and the lower traction member are configured to be located in front of a knee joint, such that a distance between the thigh region and the lower leg region may increase when the upper traction member and the lower traction member rotate in mesh.

2. The knee traction apparatus of claim 1, further comprising:
   a guide member in which a rotation axis of each of the upper traction member and the lower traction member is located.

3. The knee traction apparatus of claim 2, wherein the upper frame comprises an upper protruding element protruding inward from the upper frame,
   wherein the lower frame comprises a lower protruding element protruding inward from the lower frame,
   wherein the guide member comprises:
   a first guide groove to guide the upper protruding element inserted into the first guide groove; and
   a second guide groove to guide the lower protruding element inserted into the second guide groove, and
   wherein the upper protruding element and the first guide groove are symmetrical to the lower protruding element and the second guide groove, respectively.

4. The knee traction apparatus of claim 3, wherein the first guide groove and the second guide groove are located further behind the knee joint than the upper traction member and the lower traction member, respectively, and each have a curved shape or a linear shape.

5. The knee traction apparatus of claim 3, wherein the guide member further comprises a stopper installed in the first guide groove or the second guide groove, and a rotation angle between the upper frame and the lower frame is limited by the stopper.

6. The knee traction apparatus of claim 2, further comprising:
   a cover to protect the upper traction member, the lower traction member, or the guide member.

7. The knee traction apparatus of claim 1, wherein an end portion of each of the upper traction member and the lower traction member has a saw-toothed shape, and the upper traction member and the lower traction member rotate in mesh.

8. A knee traction apparatus, comprising:
   an upper frame provided to be worn on a thigh region, and comprising a first connector disposed in an end of the upper frame; and
   a lower frame provided to be worn on a lower leg region, and comprising a second connector rotating in contact with the first connector,
   wherein a contact area between the first connector and the second connector has an oval shape, and the first connector and the second connector rotate in contact with each other while drawing oval tracks, and
   wherein the first connector or the second connector moves toward a major axis of the oval track of the first connector or the second connector while a knee is straightened, and moves toward a minor axis of the oval track of the first connector or the second connector while the knee is bent, the knee traction apparatus, further comprising:
a guide member mounted in the first connector and the second connector, to stably guide rotation of the first connector and the second connector;
wherein the first connector comprises:
 a first protruding element protruding outward from a focal point of the first connector; and
 a third protruding element protruding inward from a central point of the first connector,
wherein the second connector comprises:
 a second protruding element protruding outward from a focal point of the second connector; and
 a fourth protruding element protruding inward from a central point of the second connector, and
wherein the guide member comprises:
 an outer guide member to connect the first protruding element and the second protruding element; and
 an inner guide member to connect the third protruding element and the fourth protruding element,
wherein the outer guide member comprises:
 a first groove into which the first protruding element is inserted; and
 a second groove into which the second protruding element is inserted,
  wherein the first groove and the second groove are aligned in the outer guide member and each have a linear shape,
wherein the inner guide member comprises:
 a third groove into which the third protruding element is inserted; and
 a fourth groove into which the fourth protruding element is inserted, and
  wherein the third groove and the fourth groove are aligned in the inner guide member and each have a linear shape.

9. The knee traction apparatus of claim 8, wherein an end portion of each of the first connector and the second connector has a saw-toothed shape, and the first connector and the second connector rotate in mesh.

10. The knee traction apparatus of claim 8, wherein the first connector further comprises:
a fifth protruding element disposed outside the first connector,
wherein the second connector further comprises:
a sixth protruding element is disposed outside the second connector, and
wherein the outer guide member further comprises:
a fifth groove into which the fifth protruding element is inserted and having a curved shape; and
a sixth groove into which the sixth protruding element is inserted and having a curved shape.

11. The knee traction apparatus of claim 8, wherein the first connector and the second connector are detachably coupled to the upper frame and the lower frame, respectively.

12. The knee traction apparatus of claim 8, further comprising:
a cover to protect the first connector, the lower second connector, and the guide member,
wherein the cover comprises a movement element connected to the first protruding element and the second protruding element on an outer surface of the cover, to visually verify rotation of the first connector and the second connector.

* * * * *